(12) United States Patent
Cohen et al.

(10) Patent No.: US 7,794,740 B2
(45) Date of Patent: Sep. 14, 2010

(54) TRANSPARENT CONCEALING COSMETIC COMPOSITIONS

(75) Inventors: Isaac D Cohen, Brikklyn, NY (US); Maryanne Ivanjesku, Huntington Station, NY (US); Yelena Mikhaylova, Smithtown, NY (US); John D Dreher, Sayville, NY (US); Sharon Mesfen, Uniondale, NY (US)

(73) Assignee: Color Access, Inc, Melville, NY (US)

( * ) Notice: Subject to any disclaimer, the term of this patent is extended or adjusted under 35 U.S.C. 154(b) by 1016 days.

(21) Appl. No.: 10/713,843

(22) Filed: Nov. 15, 2003

(65) Prior Publication Data

US 2004/0120908 A1    Jun. 24, 2004

Related U.S. Application Data

(60) Provisional application No. 60/426,608, filed on Nov. 15, 2002.

(51) Int. Cl.
*A61K 8/02* (2006.01)
(52) U.S. Cl. ................................................. 424/401
(58) Field of Classification Search .......... 424/401
See application file for complete search history.

(56) References Cited

U.S. PATENT DOCUMENTS

| 5,000,937 | A | | 3/1991 | Grollier et al. | |
| 5,486,354 | A | | 1/1996 | Defossez et al. | |
| 5,690,916 | A | | 11/1997 | Kimura et al. | |
| 5,830,485 | A | * | 11/1998 | Gueret et al. | 424/401 |
| 6,242,056 | B1 | * | 6/2001 | Spencer et al. | 427/512 |
| 6,517,628 | B1 | | 2/2003 | Pfaff et al. | |

FOREIGN PATENT DOCUMENTS

| CA | 2464692 A1 | 5/2003 |
| EP | 0701810 | 3/1996 |
| EP | 1013724 A1 | 6/2000 |
| EP | 1033126 | 9/2000 |
| EP | 1082952 | 3/2001 |
| JP | 01-224220 | 9/1989 |
| JP | 2184618 | * 7/1990 |
| JP | 2002020235 | 1/2002 |
| JP | 2002-038051 | 2/2002 |
| JP | 2002104923 | 4/2002 |
| WO | WO 01/51017 | 7/2001 |
| WO | WO02/056846 | 7/2002 |
| WO | WO 03/045345 A | 6/2003 |

OTHER PUBLICATIONS

English abstract of JP 2184618.*
PCT International Search Report; International Application No. PCT/US03/36550; Completion Date: Jun. 14, 2004; Date of Mailing: Sep. 1, 2004.
Supplmentary European Search Report; Application No./Patent No. 03786733.0-1219; PCT/US03/36550; Completion Date: Apr. 18, 2007; Mailing Date: Apr. 27, 2007.

* cited by examiner

*Primary Examiner*—San-ming Hui
(74) *Attorney, Agent, or Firm*—Mimi Y. Yang

(57) ABSTRACT

The present invention relates to topical compositions comprising (a) a transparent component; and (b) a non-interference platelet component having an average particle size of 25μ or less, the platelet exhibiting a light transmission value of about 20% to about 70%, and a light reflectance value of about 10% to about 20%. The compositions are useful in providing effective but sheer concealment to skin flaws, without the necessity of using large amounts of metal oxide pigments.

14 Claims, 1 Drawing Sheet

Terms:
$I_0$ = Incident Light Source
$R_0$ = Reflected Light (Mirror)
$T_0$ = Transmitted Light of Glass with Lacquer Coating
$R_x$ = Reflected Light of Sample
$T_x$ = Transmitted Light of Sample
$A_x$ = Absorption by the Sample
$S_x$ = Scatter not picked up by the detector
**- Above measured in LUX at 90° for Reflectance and 45° for Transmittance

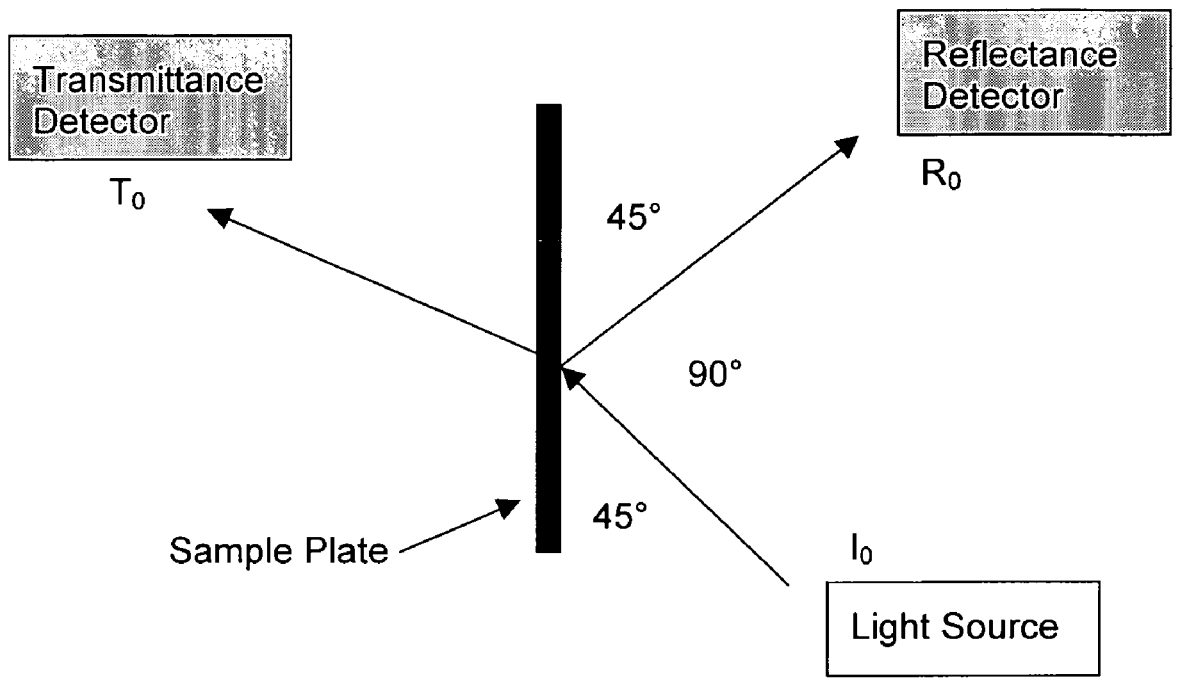

TRANSPARENT CONCEALING COSMETIC COMPOSITIONS

The instant application claims the benefit of U.S. provisional application 60/426,608, filed Nov. 15, 2002.

FIELD OF THE INVENTION

The present invention relates to compositions for topical application to the skin. In particular, the invention relates to a topical compositions useful in concealing flaws on the skin.

BACKGROUND OF THE INVENTION

While a major purpose of the use of cosmetics is to enhance or emphasize certain facial features, such as the eyes or lips, another important use is diminishing the appearance of facial or other bodily features that are less than perfect. Few consumers are blessed with flawless skin, and concealment of facial flaws is a crucial function of any truly functional makeup. The challenge of the cosmetic formulator is to provide a makeup that will mask the imperfections, and yet let the desirable aspects of the user's skin shine through. In other words, a useful concealer will hide blemishes, and yet overall leave the skin with a natural glowing appearance that is characteristic of bare, unflawed skin.

Attaining this end is not so simple. The characteristic method of concealing skin imperfections has, in the not so distant past, been to apply what is substantially a "mask", i.e., an opaque physical covering for the blemish that literally hides it from view. This has been routinely done by use of makeups that contain high levels of metal oxides, which are substantially opaque and therefore provide a fairly effective barrier to visibility of the flaw lying beneath. Although effective in concealing, this type of makeup has many drawbacks. First, they tend to be thick and heavy, as a result of the high level of pigment needed to provide physical concealment. More importantly, however, they leave the user's face with a matte, uniform, very unnatural appearance which few consumers will find desirable.

In recent years, the trend has been to develop makeups that, rather than physically masking flaws, attempt to fool the observer's eye into not seeing them. This is done by exploiting the optical properties of certain types of pigments. Various types of interference pigments, for example, reflect light in such a way as to prevent the observer's eye from seeing the blemish that lies beneath the pigment. A number of makeup compositions based on the use of interference pigments, or optical properties of other cosmetic powders, have recently been reported (e.g., U.S. Pat. No. 5,690,916; WO 01/51017) However, there continues to be a need for a makeup that provides a truly effective "concealer" effect, without the substantial use of opacifying pigments, so that a natural, transparent, flawless bare skin look is achieved.

SUMMARY OF THE INVENTION

The present invention relates to topical compositions for application to the skin comprising (a) a transparent component; and (b) a non-interference platelet component having an average particle size of 25μ or less, the platelet exhibiting a light transmission value of about 20% to about 70%, and a light reflectance value of about 10% to about 20%. The compositions, when applied to the skin, have the effect of diminishing or eliminating the appearance of skin blemishes, while permitting surrounding clear skin to retain its normal, healthy appearance.

BRIEF DESCRIPTION OF THE FIGURE

FIG. 1 illustrates diagrammatically the setup and measurement of transmittance and reflectance parameters of the invention.

DETAILED DESCRIPTION OF THE INVENTION

The present invention is predicated on the concept of using one-way mirrors on the skin to permit concealment of flaws on the skin while simultaneously allowing clear skin to shine through. One-way, or variable, mirrors are partially transparent mirrors which in practice allow individuals on one side of the mirror to perceive the glass as a window, while an individual on the other side perceive the glass as a mirror. The effect is achieved, in part, by having the reflective surface only partially coated, or "half-silvered", so that some light is transmitted through the glass, while some is reflected. The essential elements of the composition mimic the components of the mirror by providing a transparent glass component combined with a component that provides the appropriate "silvering". The present compositions therefore provide a similar result to a one way mirror, providing light reflection where needed, for example, over a dark spot on the skin to hide the spot and light transmission where needed, for example on unflawed skin to provide a sheer, transparent, natural-looking appearance. Thus, the makeup adjusts to the individual user's skin's needs, and in fact works with the user's skin: the clear skin areas provide enough light to shine through the makeup "mirror", while the blemished skin, being darker, causes the "mirror" to become more opaque in that vicinity. The overall effect is a sheer, natural-looking makeup that effectively conceals blemishes without altering the appearance of the unflawed skin. The effect is achieved by balancing components having defined properties of light transmission and light reflectance. The methods for determination of a material's capacity for transmitting or reflecting light are disclosed in Example 1 herein, and all references to "transmission" or "reflectance" in the present specification are used in the context of this methodology.

A first essential component of the composition is a transparent component. This component, in the composition and on the skin, is optically negligible, in that its function is to let everything in its vicinity, such as skin and ambient light, shine through its transparency. The term "transparent" is a relative one: the material need not be transparent in the absolute sense, but rather must be transparent in its functional environment. This is achieved by choosing a material that matches the refractive index (R.I.) of its surroundings. In practical terms, this translates to selecting a material for a powder composition that matches the refractive index of air, i.e., an R.I. of about 1. The R.I. of cosmetic oils is generally between about 1.4-1.6, and for a silicone oil-based composition, the preferred material will have an R.I. of about 1.5, which matches the R.I. of the silicone oil. The R.I. of water is between about 1.3 -1.4, and for a water-based composition, the transparent component will be selected accordingly. The transparent component as defined herein will exhibit light transmission values greater than about 70%, preferably greater than about 75%, and will not exhibit light scattering properties.

The transparent material can be any type of material that meets these criteria in the selected environment. Generally speaking, however, the most conveniently available material for this purpose is glass spheres or beads, acting as the light transmitting portion of the mirror. Any type of glass bead may be used, but it is preferred that the bead be relatively small for aesthetic reasons. Ordinarily, the spheres used should have an average diameter in the size range of preferably about 1 to about 100 microns, more preferably about 1 to about 50 microns, and most preferably about 1 to about 10 microns. The beads can be formed from any cosmetically acceptable type of glass, such as silica glass, quartz, soda lime glass, borosilicates, barium titanate, or electroconductive glass. The glass should not be coated with metal, but may be colored glass. The sphere may be hollow, which is the preferred form for use in powder compositions because of their greater transparency and an R.I. approaching 1, or they may be solid, which is the preferred for use in liquid compositions. Examples of useful hollow glass beads are "Hollow Glass Microspheres", composed of calcium aluminum borosilicate (>98%) and silica(<2%), provided by Cardre Inc., South Plainfield, N.J. Examples of useful solid glass spheres are Prizmalite™, composed of soda-lime glass, with an average particle size of about 4.5 microns, and a maximum particle size of about 13 microns, and a refractive index of about 1.51, provided by Prizmalite Industries, and further described in U.S. Pat. No. 6,242,056, the contents of which are incorporated herein by reference. The quantities of glass beads used in the compositions is not particularly critical, but they will ordinarily be used in an amount of no less than 0.1%, preferably at least about 0.5%, and in most cases, from about 1 to an amount of about 10%, with the relatively larger quantities being used in powder compositions.

The second component of the composition represents the "silvering" component of the variable mirror. This component is chosen from cosmetically acceptable, platelet, non-interference pearlescent pigments. The appropriate material for this purpose is normally a platy material that provides a continuous, sheetlike, reflective finish, rather than a sparkly, discontinuous shine. The platelet material employed does not exhibit the color travel that is characteristic of most interference pigments, and as used herein, the term "non-interference" is used to describe a pearlescent, platelet pigment that does not exhibit color change when viewed at different angles. Qualitatively, the material is typically white, or silvery white, and preferably exhibits a relatively low, non-glittering, luster. The shine without excessive sparkle is most readily achieved by use of platelets having an average (i.e., >50%) particle size of less than about 25μ. The platelet component, while not as transparent as the transparent component, should also exhibit some transparency, i.e., at least about 20% transmission of light, but generally no greater than about 70%. The preferred ranges for transmission values vary between powder and liquid compositions; for powders, transmission values are preferably about 30 to about 70%, and more preferably about 30 to about 45%, while in liquids, the transmission value is preferably about 20 to about 70%, and more preferably about 20 to about 30%. Also important, however, is its reflectance properties. The platelet material should have a reflectance value in the range of from about 10% to about 20%. Again, the preferred values will differ from powder to liquid: in a powder composition, the preferred reflectance values are from about 14 to about 20%, more preferably about 14 to about 18%, whereas for liquid compositions, the values are preferably from about 10 to about 14%, more preferably from about 10 to about 12%. Examples of useful platelets for this component are metal flakes, particularly alumina flakes. Particularly preferred alumina flake is manufactured by Merck KgaA, Darmstadt, Germany, and sold under the commercial name Xirona® Silver. This material is a relatively transparent, titanium dioxide coated alumina flake with a particle size range of about 5 to about 40 microns, but with an average particle size of about 15-22μ.

The amount of platelet component used will typically be in the range of about 0.01 to about 10%, but as will be seen below, amounts used are more appropriately discussed in terms relative to the other components of the composition.

The success of the composition is very much dependent of the interplay of transmissive and reflective properties of the essential components. As has been noted above, the absolute amounts of essential materials used is not as crucial as the overall balance between light transmission and reflecting properties of the component materials. It is possible to achieve this ratio, and thus the desired effect, with the simple combination of transparent component and platelet component, given the proper transmission and reflectance values and/or the amounts of components. It is also possible to achieve the same results in liquid and powder with the same platelet materials by adjusting the amount of platelet to achieve the optimum effect for the chosen medium. For example, a combination of glass spheres and the alumina flake material noted above can alone provide the desired effect of successfully concealing flaws while retaining the natural look of the surrounding unflawed skin. However, since the balance of transmission and reflection is important in selecting a single platelet component, it has also been determined that this balance should be applied to a combination of components. In some cases, with the choice of different platelet-type components that may be, alone, outside the desired range, or in order optimize the effect achieved with a single platelet component that does meet the requirements, it may be desirable to provide additional components that will, respectively, place the combined components into the desired transmission/reflectance range, or modify the overall effect to a more optimal range. It may also be desired to adjust the overall color of the composition out of the grayish tone that it will ordinarily take on from the essential components. In other words, it is possible, and frequently preferable, to provide a mixture of components, which although individually outside the range prescribed for the platelet component, in combination with each other, or in combination with a selected compliant platelet component, fall within the prescribed range. In order for the mixture of components to be effective, however, the overall transmission and reflectance values of the combination must fall within the range defined for the platelet component alone.

The supplemental components which serve to optimize the effect achieved by essential components clearly must also be selected with the properties of transmission and reflectance in mind, and any cosmetically acceptable material that does not substantially alter the transmission/reflectance balance, or that enhances the balance, can be used. Because the essential components, i.e. the transparent component and the platelet component, are ideally relatively transmissive, frequently it will be additional reflectance that is required to optimize the balance. Therefore, when a supplemental component is either required or desired, examples of useful materials are relatively non-transmissive i.e., light transmission values of less than about 20%, preferably in the range of about 10 to about 20%. The preferred supplemental component is a pearlescent non-interference platelet having an average particle size of less than about 50μ. One example of such a material is a small particle size bismuth oxychloride, with an average particle of about 9-15μ, available under the commercial name Biron B-50 (Rona). In a preferred embodiment, the platelet is a colorant-or pigment-containing non-interference platelet. In many cases, the color will be imparted by the presence of one or more iron oxides. As an example, one particularly useful component of this type is a dull, non-shiny silver-gray platelet. A particularly useful supplemental component is a multilayered platelet comprising mica, iron oxides, and titanium dioxide. An example of a commercially available product of this type is Colorona® Patina Silver, manufactured by Merck KgaA. This material has an average particle size range of about 18-25μ. Although the platelet just described is primarily dark gray in color, similar platelets, containing different colored organic or inorganic pigments, particularly different colored iron oxides, can be used to produce a dark component of a different color that may be useful in neutralizing colored spots on the skin, for example, green, yellow or blue to neutralize a red blemish, or red to neutralize a blue-colored blemish.

As another example of a useful supplemental component of this type is one which counteracts the grayness of the basic composition, i.e., provides more of a natural skin-tone to the composition. One particularly preferred optional component is a brown, bronze or copper-colored reflective, non-opaque pigment. Examples of useful pigments of this type of pigment are any brown platelet pigment or any reflective brown, bronze or copper-colored metal powder, such as pure copper powder having appropriate transmission and reflectance properties as described above. A particularly preferred pigment used for this purpose is a platelet-type pigment comprising predominantly iron oxide, particularly a red iron oxide, and alumina. Material of this type is commercially available, under the name Pearl Copper 1000, from Cardre Inc containing about 93% red iron oxide and about 7% alumina.

Additional useful color-providing components, which may be used in combination with the non-interference supplemental component, include interference synthetic silica flakes, particularly silica flakes coated with metal oxides. Examples of such products are silica flake coated with rutile titanium dioxide and tin (IV) oxide, such as is sold under the commercial name Xirona® Magic Mauve, conferring a lilac-red to silver to green blue color depending on viewing angle, or Xirona® Nordic Sunset, a silica flake coated with rutile titanium dioxide, which confers a silver-red to green-gold color; as well as a silica flake coated with iron oxide, such as is sold as Xirona® Indian Summer, a red-gold to bronze to green-gold. Each is available from Rona and has a particle size of 5 to 50μ. Another similar pigment is Xirona® Caribbean Blue, a combination of silica, titanium dioxide and mica. Any one or a combination of the foregoing pigments may be used to confer additional color to the composition as well as to counterbalance discolorations or uneven coloration on the skin, such as may be found, for example, in skin affected by rosacea or other skin conditions that affect skin color.

The amount of the supplemental component utilized, as with the essential components, will ordinarily be in the range of from about 0.01 to about 10%, but as mentioned above, the combination of components to achieve the desired transmission and reflectance values is more important than defining absolute values of components utilized.

Additional cosmetic materials can also be employed in the composition to enhance the effects of the essential and supplemental components, or to otherwise improve the aesthetics of the composition. It should be clear from the foregoing discussion that all additional components should be carefully selected so as to prevent interference with the transmission and reflectance values already established by the principle components. Generally speaking, although no one material is specifically prohibited for use, it is preferred that the additional components be transparent or nearly so, so as to avoid opacifying the composition to such an extent that the sheer, natural effect is lost. To the extent a somewhat opaque material may be desired for a particular purpose, it recommended for use in small amounts so as to avoid an overall opacity. As a rule, the remainder of the ingredients used in the formula should, in combination, exhibit a light transmission level in the range of from about 20 to about 70%.

One example of a useful additional component is one or more soft focus powders. The presence of these powders enhance the optical effect of the mirror components by scattering or diffusing light on the skin. Examples of such powders include, but are not limited to, powders comprising (with examples of commercially available sources) calcium aluminum borosilicate (Luxsil™), PMMA (Microsphere M-100), polyethylene (polyethylene Cl 2080), methyl methacrylate crosspolymer (Covabeads LH85), nylon-12 (Orgasol 2002 O Nat Cos C), or ethylene/acrylic acid copolymer (Flobeads EA209). These powders, when used, are present in an amount of from about 0.001% to about 20%, preferably about 1% to about 10%, by weight of the total composition.

The compositions of the invention can be used as the base for any type of cosmetic product, for example, for color cosmetics or treatment products. As a rule, treatment products will not ordinarily require the presence of additional colorants, but when used as a color cosmetic, it may be desirable to incorporate additional pigment components to create various shades of makeup. The types of pigments that are employed can be any that are ordinarily used for this purpose; for example, they may be organic, including natural colorants and synthetic monomeric and polymeric colorants. Exemplary organic pigments are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C lakes and blends thereof. Stains, such as bromo dyes and fluorescein dyes can also be employed.

The pigments can also be inorganic; inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide (white), zinc oxide and mixtures thereof. Also useful are transparent metal oxide-coated silica beads. Metal oxides, particularly iron and titanium oxides, are the most common color components of makeups, particularly foundations and concealers. However, one of the primary advantages of the present system is that it permits the creation of a highly effective concealer without the presence of large amounts of metal oxide pigments, which render the makeup heavier and more opaque, and thus leave the skin looking somewhat unnatural. In a typical concealer, metal oxides will typically be present in an amount of at least about 15-25%, whereas in the present compositions, substantially equivalent effects can be achieved with much less. Indeed, an acceptable concealing effect can be achieved in a product having no metal oxide pigments at all. However, where it is preferred to produce a more traditional makeup-type concealer, the present compositions can contain greater than zero to about 15% metal oxide, and frequently contain only about 1 to about 5% metal oxides, the lower end of this range being used in powder compositions. In a preferred embodiment of the invention, one or more of the metal oxides used are transparent, typically of very small (i.e., submicron) particle size or nanopigments. Where traditional, rather than small particle size pigments are used, the lower end of the range will be preferred, whereas with the transparent pigments, a higher level can be used without interfering with the sheerness of the composition.

The compositions may also benefit from the incorporation of one or more plate-like, non-spherical powders that confer some luster, but not an overt shine. To achieve the maximum benefit of this effect, the powder is preferably uncolored and has an average particle size that is relatively small, about 2 to 50μ, more preferably about 3-20μ, most preferably about 3 to 6μ. Examples of such powders include, but are not limited to, bismuth oxychloride, boron nitride, barium sulfate, mica, sericite, muscovite, synthetic mica, titanium oxide coated mica, titanium oxide coated bismuth oxychloride, titanium oxide coated talc, platelet iron oxides, metal powders such as aluminum, lauroyl lysine and platelet talc, to the extent these materials, as used in the product, do not meet the light transmission requirements described above. These powders, when used, are essentially present as fillers, and therefore may make up the bulk of the remainder of the product outside the essential and preferred components named above, and therefore the amount may be any amount needed to make up the remainder of the composition, again, provided they are used in amounts that permit retention of sheerness of the product Preferably transmission should be at least about 50% overall, and particularly preferred is a value of at least about 75%. It should also be noted that, with regard to any pigments or powders used in the composition, these may or may not be surface-treated.

As has been repeated throughout the specification, the amounts provided of each of the essential and preferred components are provided as general guidelines only. The determination of relative amounts of each component is secondary to the determination of whether a component will provide, in its chosen context, the necessary light transmission and light reflectance properties as defined in detail above. The skilled artisan will readily recognize, in view of the guidance provided above, that amounts of materials falling within the prescribed transmission/reflectance standards can be combined in various amounts to optimize the final product, and particularly to account for the differences in vehicles between a powder product and a liquid product. Thus, the skilled artisan can routinely modify their proportions to achieve a functional product by simply ensuring the final combination meets the requirements of light transmission and reflectance as described herein. As a guideline, and as shown in the various examples herein, a useful range of transmission to reflectance is in the range of 1-5:1, and preferably 2-3:1.

The compositions may also incorporate other components that are typically used in cosmetic formulations, for example, active components such as antioxidants, vitamins, sunscreens, self-tanning agents, anti-dry skin agents, whitening agents, anti-aging agents, as well as non-active components emollients, moisturizers, fillers, thickeners, emulsifiers, suspending agents, and the like. A comprehensive list of cosmetic ingredients can be found in the *International Cosmetic Ingredient Dictionary and Handbook*, Ninth Edition, published by the Cosmetics, Toiletries and Fragrance Association; its contents are incorporated herein by reference. The compositions can be used in any situation in which it is desired to conceal a skin flaw. Examples of this include, but are not limited to, application to skin discolorations, unevenness of skin tone, rosacea, dark shadows, lines and wrinkles. A particularly useful application of these compositions as a treatment product is as a whitening product with or without the addition of a whitening active. The composition alone, without a whitening active, provides substantially the same effect as a traditional whitening composition, in that it conceals the appearance of dark spots, albeit without the actual removal of the spot from the skin, but with an immediately observable effect. Thus the compositions provide an interesting alternative, or companion treatment, to compositions containing a chemical whitener.

The form of the vehicle is not critical, and can be any that is typically used for topical application. The vehicle can be wet or dry, liquid or solid, anhydrous or aqueous, and it can be an emulsion(oil-in-water, water-in-oil), pressed powder, loose powder, a hot pour, a suspension, or spray. In essence, the vehicle may take any form that is useful for application to the skin. The art of topical formulation is well developed, and methodologies and principles are disclosed, for example, in Remington's Pharmaceutical Sciences, A. R. Gennaro, ed., 20$^{th}$ Edition, 2000, or Harry's Cosmeticology, M. Rieger, ed. 8$^{th}$ edition, 2000; the contents of each of these documents are incorporated herein by reference. A particularly useful form of the composition, however, is a water and silicone emulsion, preferably a water-in-silicone emulsion, with the silicone phase preferably containing cyclomethicone, dimethicone, phenyltrimethicone, or any combination of these. In this form, it is particularly preferred that the composition also contain at least one silicone elastomer in the silicone phase. Any silicone elastomer may be used; however, it is particularly preferred to utilize one or more elastomers such as polysilicone-11 or a dimethicone crosspolymer, for example, a dimethicone/vinyl dimethicone crosspolymer, a dimethicone/phenyl vinyl dimethicone crosspolymer, a lauryl dimethicone/vinyl dimethicone crosspolymer, a lauryl dimethicone/copolyol crosspolymer, or a dimethicone/copolyol crosspolymer. Elastomers of this type are available commercially from Grant Industries or Shin-Etsu, in their KSG series. When used, the silicone elastomer is used in an amount of from about 1 to about 10%, preferably in an amount of about 4 to 8% by weight.

As already noted, the compositions can be used as a treatment product, containing skin care actives, as a cream, lotion, gel, powder, stick, spray, and the like, or it can be used as a color cosmetic, in the form of a lipstick, lip gloss, lipliner, eyeshadow, blush, foundation, concealer, eyeliner, or any other typical color product.

The present invention is further illustrated by the following non-limiting examples.

EXAMPLE 1

This example describes the methodology employed for determining the amount of light transmission and light reflection exhibited by a candidate cosmetic material(s). FIG. 1 illustrates the procedure diagrammatically.

A. Sample Preparation.

Samples to be tested are prepared by incorporating the material of interest into a clear nail lacquer base, available from Kirker Enterprises, Paterson, N.J. As an initial test sample, testing of a sample containing 5% of the test material is recommended. A 10 cm×10 cm×2 mm glass plate is tared, and 2 g of sample is added onto the glass. The sample is drawn down the glass with another glass plate. The sample-containing glass plate is reweighed. 1-1.2 g of sample should remain on the glass as an even film.

B. Equipment.

Nicholas Illuminator, Fisher Product No. BL 31-33-05-28; this illuminator projects a 35 mm spot @ 2800 Kelvin Fisher Scientific Foot Candle Meter, set on I×10 lux, FC Fast 2000

C. Procedure.

(i) Light Transmission Measurement

An optical bench is sent up, on which the light source is placed one inch away from the sample at a 45° angle. The light detector is placed on the opposite side of the glass from the light source, exactly one inch away from the sample. The detector should be at a 45° angle from the sample, and aligned horizontally with the light source. The light source is turned on and left until a steady reading is registered on the detector. Once this point is reached, a control reading, $T_0$, is taken on a lacquer coated glass without the test material present. The test reading, $T_x$, is then taken of the lacquer coated glass with the test material. Percentage transmission is calculated according to the following equation: $100(T_x/T_0)=\%$ transmission. Preferably, at least two of each of the readings are made, and the average of the two tests taken to get a reliable indication of the transmission.

(ii) Light Reflectance Measurement

The light source is placed one inch away from the sample at a 45° angle. The detector is placed on the same side of the sample as the light source, one inch away from the sample at a 45° angle. The light from the light source shines on the sample and reflects onto the detector. A control reading, $R_0$, is taken by shining the light source on a plain mirror, and recording the reflectance reading on the detector. The test reading, $R_x$, is conducted in the same way, but using the sample-coated glass, shining the light source on the sample and recording the reflectance reading on the detector. Percentage reflectance is calculated according to the following equation:

$100(R_0/R_x)=\%$ reflectance.]

Table 1 illustrates sample readings taken on candidate materials for use in the present compositions:

TABLE 1

Measurements of transmission and reflectance of a variety of cosmetic products.

|  | Mixture | % | Raw | | Corrected | |
|---|---|---|---|---|---|---|
|  |  |  | Tx | Rx | (Tx/To) 100 | (Rx/Ro) 100 |
|  | Xirona | 5 | 106 | 44 | 41 | 16.9 |
| Powder | Xirona | 2 | 91 | 43 | 35 | 16.5 |
| Optimum | Patina Silver | 0.5 |  |  |  |  |
|  | Copper pearl | 0.5 |  |  |  |  |
| Powder | Xirona | 1 | 155 | 34 | 60 | 16 |
| upper | Patina Silver | 0.1 |  |  |  |  |
| limit | Copper pearl | 0.5 |  |  |  |  |
| Liquid | Xirona* | 2 | 67 | 27 | 26 | 10.4 |
| optimum | Patina silver*** | 1 |  |  |  |  |
|  | Copper pearl**** | 0.3 |  |  |  |  |
|  | Biron B-50 | 3 |  |  |  |  |
| lower limit | Flamenco superpearl | 5 | 58 | 33 | 22 | 12.7 |
|  | 100% light (T$_o$) |  | 260 |  |  |  |
|  | Reflected Light Mirror (R$_o$) |  |  | 260 |  |  |
|  | Solid glass microsphere** | 5 | 203 | 21 | 78.7 | 8 |
|  | Copper pearl | 5 | 22 | 39 | 8.5 | 15 |
|  | Talc 141 | 5 | 86 |  | 33 |  |

*Xirona ® silver, Merck
**Prizmalite ™ solid microspheres
***Colorona ® patina silver, Merck
****Cardre Pearl Copper 1000

EXAMPLE 2

This describes a liquid foundation/concealer of the present invention.

| Material | Weight % |
|---|---|
| Phase I | |
| Phenyl trimethicone/quaternium-18 hectorite/triethyl citrate | 2.00 |
| phenyl trimethicone | 6.00 |
| cetyl PEG/PPG-10/1 dimethicone/polyglyceryl-4-isostearate/hexyl laurate | 0.50 |

-continued

| Material | Weight % |
|---|---|
| propyl paraben | 0.10 |
| titanium dioxide/triethoxycaprylyl silane | 1.86 |
| yellow iron oxide | 0.92 |
| red iron oxide | 0.157 |
| black iron oxide/triethoxycaprylyl silane | 0.053 |
| ultrafine titanium dioxide | 2.00 |
| Phase II | |
| cyclomethicone | 7.50 |
| Phase III | |
| Cyclomethicone | 15.00 |
| Bis-PEG/PPG-14/14 dimethicone/cyclomethicone | 3.00 |
| Phase IV | |
| Purified water | 26.10 |
| 1,3-butylene glycol | 7.00 |
| laureth-7 | 0.15 |
| phenoxyethanol | 0.70 |
| magnesium sulfate | 2.00 |
| Phase V | |
| Alumina/titanium dioxide* | 2.00 |

-continued

| Material | Weight % |
|---|---|
| Fused amorphous silica & inorganic oxides** | 1.00 |
| Mica/iron oxides/titanium dioxide*** | 0.50 |
| Mica/magnesium myristate | 4.00 |
| Iron oxides/alumina**** | 0.50 |

*Xirona ® silver, Merck
**Prizmalite ™ solid microspheres
***Colorona ® patina silver, Merck
****Cardre Pearl Copper 1000

EXAMPLE 3

This example illustrates another liquid concealer of the invention.

| Material | Weight % |
| --- | --- |
| Phase I | |
| Water | QS |
| Hyaluronic acid(1%) | 11.25 |
| Polysorbate 40 | 0.60 |
| Phase II | |
| Cyclomethicone/polysilicone-11(6.5%) | 75.00 |
| Phase III | |
| PEG-10 dimethicone | 2.50 |
| Phase IV | |
| Methyl paraben | 0.25 |
| Phenoxyethanol | 0.60 |
| Water/sodium hydroxide (30%) | 0.025 |
| Phase V | |
| Alumina/titanium dioxide* | 0.60 |
| Fused amorphous silica & inorganic oxides** | 0.60 |
| Mica/iron oxides/titanium dioxide/triethoxycaprylsilane*** | 0.012 |
| Mica/magnesium myristate | 0.60 |
| Iron oxides/alumina**** | 0.06 |
| Titanium dioxide/silica/mica | 1.90 |
| HDI/trimethylol hexyllactone crosspolymer | 1.25 |
| Bismuth oxychloride | 0.60 |

*Xirona ® silver, Merck
**Prizmalite ™ solid microspheres
***Colorona ® patina silver, Merck
****Cardre Pearl Copper 1000

EXAMPLE 4

This example illustrates a makeup/concealer powder composition of the present invention, containing glass beads and a platelet component.

| Material | Weight % |
| --- | --- |
| Phase I | |
| Mica/magnesium myristate | 40.28 |
| Lauroyl lysine | 8.87 |
| Zinc stearate | 2.00 |
| Transparent yellow iron oxide/triethoxycaprylylsilane | 2.00 |
| Transparent red iron oxide/triethoxycaprylylsilane | 1.00 |
| Black iron oxide | 0.50 |
| Methyl paraben | 0.30 |
| Butyl paraben | 0.05 |
| Propyl paraben | 0.10 |
| Potassium sorbate | 0.20 |
| Octyl palmitate | 0.20 |
| Cetyl octanoate | 0.20 |
| Phase II | |
| Mica/magnesium myristate | 17.20 |
| Mica/lecithin | 15.50 |
| Calcium aluminum borosilicate/silica* | 5.60 |
| Alumina/titanium dioxide | 5.00 |
| Cetyl octanoate | 0.50 |
| Octyl palmitate | 0.50 |

*Cadre hollow glass microspheres

EXAMPLE 5

This example illustrates an additional makeup/concealer powder composition of the invention containing glass beads, a platelet component, and a supplemental component.

| Material | Weight % |
| --- | --- |
| Phase I | |
| Mica/magnesium myristate | 43.28 |
| Lauroyl lysine | 5.00 |
| Zinc stearate | 2.00 |
| Transparent yellow iron oxide/triethoxycaprylylsilane | 2.00 |
| Transparent red iron oxide/triethoxycaprylylsilane | 1.00 |
| Black iron oxide | 0.50 |
| Methyl paraben | 0.30 |
| Butyl paraben | 0.05 |
| Propyl paraben | 0.10 |
| Potassium sorbate | 0.20 |
| Octyl palmitate | 0.20 |
| Cetyl octanoate | 0.20 |
| Phase II | |
| Mica/magnesium myristate | 17.20 |
| Mica/lecithin | 15.50 |
| Calcium aluminum borosilicate/silica | 5.60 |
| Alumina/titanium dioxide | 2.00 |
| Mica/iron oxides/titanium dioxide | 1.00 |
| Iron oxides/alumina | 0.20 |
| Bismuth oxychloride* | 2.67 |
| Cetyl octanoate | 0.50 |
| Octyl palmitate | 0.50 |

*Biron B-50, Rona

EXAMPLE 6

This example shows a whitening treatment product of the invention, containing no pigment.

| Material | Weight % |
| --- | --- |
| Phase I | |
| Mica/magnesium myristate | 40.28 |
| Lauroyl lysine | 8.07 |
| Zinc stearate | 2.00 |
| Methyl paraben | 0.30 |
| Butyl paraben | 0.05 |
| Propyl paraben | 0.10 |
| Potassium sorbate | 0.20 |
| Octyl palmitate | 0.20 |
| Cetyl octanoate | 0.20 |
| Phase II | |
| Mica/magnesium myristate | 17.20 |
| Mica/lecithin | 15.50 |
| Calcium aluminum borosilicate/silica | 5.60 |
| Alumina/titanium dioxide | 5.00 |
| Iron oxides/alumina | 0.30 |
| Bismuth oxychloride | 3.00 |
| Mica/iron oxides/titanium dioxide | 1.00 |
| Cetyl octanoate | 0.50 |
| Octyl palmitate | 0.50 |

EXAMPLE 7

This example shows the efficacy of a composition of the invention in concealing skin flaws while leaving unflawed skin looking clean and natural.

Efficacy is determined by measuring the color of clean skin and comparing it with the color of skin with makeup on, as well as with the color of an age spot. The panelist is instructed to wear no makeup or moisturizer on the day of testing. Evaluations are carried out before product application (baseline) and immediately after product application. Close-up photos of the right and left face are taken using a Nikon M3 digital camera. The panelist's head is placed on a head rest to insure reproducibility. The camera is positioned two feet from the panelist at an F stop of 32. Photos are evaluated via Photoshop 6.1. The color channel (RGB) is changed to LAB color channel. The L* (reflectance) values are determined and compared on different areas of the face. The L* values are most relevant to the present demonstration, as this parameter registers light vs. dark.

In comparing the L* value of clean skin to the L* value of the same skin with makeup, the closer the ratio between the values is to 1, the more similar in color the skin with makeup is to the clear skin. In the foregoing example, the ratio of clean skin to made-up skin is 0.98. In comparing the age spot without makeup compared to the same spot with makeup, the further the ratio is from 1, the larger the color difference between the age spot on the clear skin and the same age spot covered with makeup. The ratio of age spot on clear skin to age spot on made-up skin is 1.09. In measuring the ratios between surrounding skin and the age spot, the closer the ratio is to 1, the more similar the skin and the age spot are in color. When calculating the ratio of clean skin to the age spot, the ratio is 0.86, while the ratio of made-up skin to the age spot is 0.96.

These results show that the composition of the present invention is highly effective in reducing the appearance of, or concealing, a facial flaw, while at the same time leaving the skin bearing the makeup appearing substantially the same as clean skin without makeup. In other words, the makeup applied to the entire face enables the concealment of a dark spot while leaving the remainder of the skin appearing fresh, natural, and unmade-up.

What we claim is:

1. A cosmetic composition for topical application to the skin comprising (a) a transparent component having a light transmission value of greater than about 70% and an average particle size of about 1 micron to about 10 microns; (b) a non-interference platelet component having an average particle size of about 15 microns to about 22 microns, the platelet exhibiting a light transmission value of about 20% to about 70%, and a light reflectance value of about 10% to about 20%.

2. The composition of claim 1 which further comprises at least one supplemental component (c) which is a non-interference platelet component having a light transmission value of less than about 20%.

3. The composition of claim 1 in which the transparent component is a glass bead or microsphere.

4. The composition of claim 1 in which the platelet (b) is an alumina flake.

5. The composition of claim 1 in which the platelet is a titanium dioxide coated alumina flake.

6. The composition of claim 2 in which the non-interference component (c) is a pearlescent platelet having an average particle size of less than about 50μ.

7. The composition of claim 6 in which the non-interference component is bismuth oxychloride.

8. The composition of claim 6 in which the platelet (c) comprises mica, at lease one iron oxide and titanium dioxide.

9. The composition of claim 6 in which the platelet (c) is a metallic platelet comprising iron oxide and alumina.

10. The composition of claim 2 which comprises an additional supplemental component (d) which is an interference silica flake pigment.

11. The composition of claim 1 comprising (a) a glass bead or microsphere having an average particle size of about 1 micron to about 10 microns; (b) a non-interference platelet having an average particle size of about 15 microns to about 22 microns, the platelet exhibiting a light transmission value of about 20% to about 70%, and a light reflectance value of about 10% to about 20%; and optionally (c) a non-interference pearlescent or metallic platelet having a light transmission value of less than about 20% and (d) an interference silica flake pigment.

12. The composition of claim 1 which comprises at least one metal oxide pigment in an amount of less than about 15%.

13. The composition of claim 12 in which the metal oxide is a nanopigment.

14. The composition of claim 1 which is a whitening product.

* * * * *